US012653927B2

(12) United States Patent
Schankereli

(10) Patent No.: US 12,653,927 B2
(45) Date of Patent: Jun. 16, 2026

(54) INTESTINAL TISSUE ENHANCED WITH THERAPEUTIC SALTS

(71) Applicant: Avalon Medical, Inc., Stillwater, MN (US)

(72) Inventor: Kemal Schankereli, Stillwater, MN (US)

(73) Assignee: Avalon Medical, Inc., Stillwater, MN (US)

( * ) Notice: Subject to any disclaimer, the term of this patent is extended or adjusted under 35 U.S.C. 154(b) by 948 days.

(21) Appl. No.: 17/040,499

(22) PCT Filed: Mar. 23, 2019

(86) PCT No.: PCT/US2019/023786
§ 371 (c)(1),
(2) Date: Sep. 22, 2020

(87) PCT Pub. No.: WO2019/190944
PCT Pub. Date: Oct. 3, 2019

(65) Prior Publication Data
US 2021/0023272 A1    Jan. 28, 2021

Related U.S. Application Data

(60) Provisional application No. 62/647,642, filed on Mar. 24, 2018.

(51) Int. Cl.
| | |
|---|---|
| *A61K 35/37* | (2015.01) |
| *A61K 33/08* | (2006.01) |
| *A61K 33/22* | (2006.01) |
| *A61K 33/30* | (2006.01) |
| *A61K 33/34* | (2006.01) |
| *A61K 33/42* | (2006.01) |
| *A61K 35/38* | (2015.01) |
| *A61L 27/36* | (2006.01) |
| *A61L 27/54* | (2006.01) |
| *A61P 17/02* | (2006.01) |
| *A61P 31/00* | (2006.01) |

(52) U.S. Cl.
CPC .......... *A61L 27/3687* (2013.01); *A61K 33/08* (2013.01); *A61K 33/22* (2013.01); *A61K 33/30* (2013.01); *A61K 33/34* (2013.01); *A61K 33/42* (2013.01); *A61K 35/38* (2013.01); *A61L 27/3629* (2013.01); *A61L 27/54* (2013.01); *A61P 17/02* (2018.01); *A61P 31/00* (2018.01); *A61L 2300/102* (2013.01); *A61L 2300/406* (2013.01); *A61L 2300/412* (2013.01); *A61L 2430/22* (2013.01); *A61L 2430/40* (2013.01)

(58) Field of Classification Search
None
See application file for complete search history.

(56) References Cited

U.S. PATENT DOCUMENTS

| | | | | |
|---|---|---|---|---|
| 8,173,154 B2 * | 5/2012 | Jung | ..................... | A61F 13/069 |
| | | | | 424/673 |
| 8,415,159 B2 | 4/2013 | Ward et al. | | |
| 2016/0325010 A1 * | 11/2016 | Liebler | .................. | A61L 24/08 |

FOREIGN PATENT DOCUMENTS

| | | |
|---|---|---|
| WO | 96/24364 A2 | 8/1996 |

OTHER PUBLICATIONS

Zhao et al. (2015) Biomaterials 53: 379-391. (Year: 2015).*
Agren et al. (2007) Lower Extremity Wounds 6(2): 82-97. (Year: 2007).*
Dalisson et al. (2019) Adv. Healthcare Mater. 8, 1900764 (22 pages). (Year: 2019).*
Hodde et al. (2007) Am. J. Clin. Dermatol. 8(2): 61-66. (Year: 2007).*
Kornblatt et al. (2016) J. Inorganic Biol. 161: 1-8. (Year: 2016).*
Sedighi-Pirsaraei et al. (2024) Frontiers in Bioengineering and Biotechnology, 12: 1475584 (18 pages) (Year: 2024).*
Wang et al. (2022) Carbohydrate Polymers 291: 119588 (11 pages). (Year: 2022).*
Borkow, G. et al., "Copper oxide impregnated wound dressing: biocidal and safety studies", Wounds, vol. 22, No. 12, Dec. 1, 2010, pp. 301-310.
Database GNPD [Online] Mintel, anonymous: "Mango Tangerine Dietary Supplement Fizzy Drink", XP093109441, Database accession No. 4252381, Sep. 5, 2016.
Database GNPD [Online] Mintel, anonymous: "Total Nutrition Drink", XP093109452, Database accession No. 10060217, Jun. 3, 1999.
International Preliminary Report on Patentability received for PCT application No. PCT/US19/23786, mailed on Oct. 8, 2020, 10 pages.
International search Report and written opinion received for PCT application No. PCT/US19/23786, mailed on May 17, 2019, 11 pages.
Leo N. M. et al., "An Overview of Clinical and Health Economic Evidence Regarding Porcine Small Intestine Submucosa Extracellular Matrix in the Management of Chronic Wounds and Burns", Ostomy Wound Management, vol. 63, No. 12, Dec. 1, 2017, pp. 38-47.
Nzietchueng, R. M. et al., "Mechanisms implicated in the effects of boron on wound healing", Journal Of Trace Elements In Medicine And Biology, vol. 16, No. 4, Jan. 1, 2002, pp. 239-244.
Zhao, S. et al., "Wound dressings composed of copper-doped borate bioactive glass microfibers stimulate angiogenesis and heal full-thickness skin defects in a rodent model", Biomaterials., vol. 53, 2015, pp. 379-391.

* cited by examiner

*Primary Examiner* — Russell G Fiebig
(74) *Attorney, Agent, or Firm* — Workman Nydegger

(57) ABSTRACT

The present invention is product and method for treating wounds, or enhancing wound healing, by contacting the wound with biomaterial or tissue that has been treated with a boron and copper composition.

20 Claims, No Drawings

INTESTINAL TISSUE ENHANCED WITH THERAPEUTIC SALTS

I. FIELD OF THE INVENTION

This invention relates to a composition, method, and/or system for treating tissue or biomaterial to enhance its biological and therapeutic properties; and to the use of the treated tissue or biomaterial to treat a wound or incision site.

This invention also relates to methods for preparing the small intestinal mucosa (SIS), and the therapeutic use of the treated SIS.

II. BACKGROUND OF THE INVENTION

Small Intestine Submucosa (SIS) tissue has been demonstrated to be an effective material for the treatment of wounds. SIS tissue contains, cytokines and mitogens which will enhance cellular ingrowth because these act as growth factors. The resultant tissue ingrowth enhances the healing rate of wounds.

One concern associated to the use of SIS relates to the potential for infection. While SIS tissue has been indicated to be more infection resistant than crosslinked tissues (such as glutaraldehyde tanned pericardium), its use in extreme wound cases, which often involve sepsis, merits caution. Thus, it would be advantageous to prepare, provide and/or use SIS tissue that demonstrates enhanced tissue ingrowth properties and/or reduced advent of infection.

III. SUMMARY OF THE INVENTION

This invention provides a SIS tissue with 1) enhanced tissue ingrowth properties and 2) reduced potential for infection while maintaining physical properties such that it remains useful as an implant device.

Tissue processed in this manner will have unique properties. In particular, the tissue will have retained its mitogenic and cytogenic activity since these factors will be retained throughout the manufacturing process. Further, these tissues have been shown to be non-allergenic, low-allergenic, and low or non-thrombogenic.

Tissue or biomaterial is processed, in accordance with the present invention, by exposing the tissue/biomaterial to an electrolyte solution comprising a source or boron ions and a source or copper ions.

The inventor has shown that tissues treated as described herein, particularly SIS tissues, exhibit added beneficial properties, including but not limited to increased resistance to infection, improved/faster healing time, and improved/faster healing quality. The inventor has shown that the electrolyte solution raises the pH of the extracellular (e.g., donor) tissue onto which it has been applied. The increased localized pH change inhibits microbial growth. Tissue that has been soaked in an electrolyte solution of the present invention will be infused with the elements contained in the solution. Lyophilized tissue exposed to an aqueous media will release the ions within it and subsequently the surrounding media will temporarily exhibit an elevated pH.

Further, tissue which has been processed in this manner contains levels of the elemental copper. Copper has been demonstrated to increase vascularization via capillary bed formation. Increased vascularization increases wound healing. For example, IUD devices incorporate copper. Small amounts of copper released by these devices have been shown to be very effective in stimulating capillary bed formation. In the case of uterine endometrium, copper and stimulated capillary bed formation was sufficient to inhibit anchoring of a fertilized egg, thus preventing pregnancy.

Also, tissue that has been processed as described herein promotes remodeling at the wound or implant site. Remodeling as used herein refers to the production of host tissue to replace implanted material and/or to the production of host tissue and structural proteins (e.g., collagen and cells) at the wound site.

The formulations of the present invention have been found to be antibiotic, effective against both gram-negative and gram-positive microbes; and antimycotic, effective against a broad range of fungi.

An embodiment of the invention is a wound treatment or an implant produced using a process as described herein.

Another embodiment is a method of treating a wound using the tissue processed as described herein. In some embodiments, the method of treating a wound includes veterinary applications, e.g., treating wounds in an animal such as a dog, cat, cow, horse, or pig.

While the tissue or biomaterial treated as described below may find many uses and applications, the inventor has found that the treated tissue or treated biomaterial exhibits multiple physical and biological characteristics that make it particularly suitable for treating wounds in both animals and humans.

With the following enabling description of the drawings, the apparatus should become evident to a person of ordinary skill in the art.

IV. BRIEF DESCRIPTION OF THE FIGURES

Not applicable.

V. DETAILED DESCRIPTION OF THE INVENTION

The present invention involves treating tissue so that the treated tissue is effective in the treatment of wounds. The tissue is treated with an electrolyte composition comprising a source or boron ions and a source of copper ions.

An embodiment of the invention involves the use of submucosa tissue; treating the submucosa tissue with one or more antibiotic agents and one or more antimycotic agents; and treating the treated tissue with an electrolyte solution as described in more detail below.

Suitable animal or human tissue includes but is not limited to tissues or biomaterial that contains an extracellular matrix (ECM). Preferred tissues or biomaterial are naturally derived collagenous ECMs isolated from human or animal sources. The most preferred materials and tissues are submucosa, renal capsule membrane, amnion, dura mater, pericardium, serosa, and peritoneum or basement membrane materials. Submucosa includes but is not limited to small intestinal submucosa (SIS), stomach mucosa, urinary bladder submucosa, or uterine submucosa, each of these derived or obtained from a human or animal.

Submucosa tissue, as used herein, refers to the layer of tissue beneath a mucous membrane, or the layer of connective tissue below the tunica mucosa. It is intended that the present invention should not be limited by the source of the submucosa. Submucosa tissue may be found from a variety of internal organs, including but not limited to bronchi, esophagus, small intestine, large intestine, pharynx, stomach, and bladder. Submucosa tissue may be found in a variety of mammals, including but not limited to ovine, equine, porcine, and capeine.

The preferred tissue is small intestine submucosa (SIS), more preferably porcine SIS. One skilled in the art will recognize that SIS is typically defined by the animal or source of the tissue. In humans, the intestine wall comprises seven layers, the outermost tissue layer which is mesenteric tissues. Layers 5-7 are sometimes referred to as the tunica mucosa, comprising layer five, the lamina muscularis mucosa (typically smooth muscle cells); layer six, the stratum compactum (typically acellular collagen and elastin fibers); and layer seven, the lamina epithelialis mucosa and its lamina propria.

In some embodiments of the invention, the preferred tissue is the tunica submucosa; in some embodiments, the tunica submucosa comprises layers five through seven, sometimes collectively referred to as SIS.

Typically, the preferred source of the tissue is the jejunum, ilium, or combinations thereof. Upon removal from the source species, the tissue may be soaked in physiologic saline.

One skilled in the art will recognize that the raw or untreated tissue may be treated to reduce its bioburden. Reducing bioburden includes, but is not limited to treating the tissue with an antibiotic, an antimycotic, or combinations thereof.

In accordance with a preferred process of the present invention, the raw tissue is treated with both an antibiotic and an antimycotic.

Allographs or allographic sources are prepared from intestinal tissue removed/obtained from donors of the same species. Heterographic sources may be used and processed as described herein from, for example, feline, canine, porcine, or bovine intestinal tissue. One skilled in the art will recognize that minimal morphological differences have been found in intestinal tissues from different species. For example, human intestinal tissue is histologically almost identical to canine intestinal tissue.

The tissue or biomaterial may retain growth factors or other bioactive components native to the source material. For example, submucosa may include one or more growth factors (e.g., FGF-2, TGF-beta, EGF, and/or PDGF); heparin, heparin sulfate; hyaluronic acid; fibronectin, as well as other growth factors or bioactive components.

For some embodiments, the inventor has found that using tissue from larger animals, therefore using larger tissue, may be beneficial. One skilled in the art will recognize that for some uses and treatment steps, larger tissue is easier to process.

The tissue or biomaterial can be used alone, or may be used in combination with one or more additional bioactive or pharmacological agents. Exemplary additional agents include but are not limited to physiologically compatible minerals; growth factors; antibiotics; antimycotics; chemotherapeutic agents; antigens and/or antibodies; genetic material; enzymes; and hormones.

In the disclosure that follows, "submucosa tissue" or SIS is used, but the invention should not be limited thereby. As noted above, other tissues and/or biomaterial may be used in the practice of this invention.

In accordance with the present invention, the submucosa tissue is harvested and cleaned using well known techniques. The harvested tissue is then treated with an antibiotic solution. The antibiotic solution, as used herein, may be any solution that contains one or more antibiotics. The preferred solution also contains one or more antimycotics. Preferred antibiotics include, but are not limited to penicillin and streptomycin. Any form of antibiotic may be used, including but not limited to salts, sulfates, etc.

Preferred antimycotics include but are not limited to amphotericin B. Any form of antimycotic may be used, including but not limited to salts, sulfates, etc.

The tissue should be treated with the antibiotic/antimycotic solution for a sufficient period to mediate, reduce, kill, or destroy microbial function. One skilled in the art will recognize that the period or time required to achieve this result may vary based on the specific reagents and/or reaction conditions. The inventors have found that treating the submucosa for greater than about 15 hours is effective, but the invention should not be limited thereby. One skilled in the art will recognize that other treatment periods may be beneficial, typically depending on the source tissue, the source and type of antimicrobial solution(s), and the intended use of the treated tissue.

In accordance with the present invention, the tissue is then soaked in solution comprising a source of boron ions and a source of copper ions. Typically this solution is an electrolyte or salt solution. The composition containing the boron and copper ions will be referred to as the treatment solution and the tissue will be referred to as the treated tissue.

A treatment composition of the present invention comprises a source of boron ions, as noted above. Any source and amount of boron ions may be used. A preferred source of boron ions is a borate, more preferably a borate oxide. The amount of boron ions present in the composition may range from about 1% to about 80%, preferably from about 30% to about 70%, more preferably from about 45% to about 60%. A commercially available source of boron ions comprises about 51%, as shown in Example 1.

A treatment composition of the present invention comprises a source of copper ions, as noted above. Any source and amount of copper ions may be used. A preferred source of copper ions is a soluble copper composition, more preferably a copper oxide or copper hydrochloride. The amount of copper ions present in the composition may range from about 0.01% to about 5.0%, preferably from about 0.05% to about 3.0%, more preferably from about 0.1% to about 1%. A commercially available source of copper ions comprises about 0.4%, as shown in Example 1.

As used herein any salt solution containing boron and copper may be effective within the present invention. The inventors have found that borate base bioceramic salt solutions are effective.

A treatment composition of the present invention may also include additional chemical or ions. One skilled in the art will recognize that a wide variety and amount of additional substances may be used in the practice of this invention. Exemplary additional ingredients include but are not limited to a source of calcium; a source of potassium; a source a magnesium; a source of sodium; a source of phosphorus; ionic forms or any of the above; and oxide forms of any of the above. A treatment composition of the present invention may further include a source of strontium; a source of zinc; a source of iron; ionic forms of strontium, zinc, and/or iron; and oxide forms of strontium, zinc, and/or iron; and any of the ingredients listed above alone or in any combination.

Any source and amount of calcium or calcium may be used. A preferred source of calcium ions is a soluble calcium composition, more preferably a calcium oxide. The amount of calcium ions present in the composition may range from about 1% to about 50%, preferably from about 10% to about 40%, more preferably from about 15% to about 25%. A commercially available source of calcium ions comprises about 20%, as shown in Example 1.

Any source and amount of phosphorus or phosphorus ions may be used. A preferred source of phosphorus ions is a soluble phosphorus composition, more preferably a phosphorus oxide. The amount of phosphorus ions present in the composition may range from about 1% to about 30%, preferably from about 5% to about 20%, more preferably from about 8% to about 15%. A commercially available source of phosphorus ions comprises about 12%, as shown in Example 1.

Any source and amount of magnesium or magnesium ions may be used. A preferred source of magnesium ions is a soluble magnesium composition, more preferably a magnesium oxide. The amount of magnesium ions present in the composition may range from about 1% to about 20%, preferably from about 2% to about 10%, more preferably from about 3% to about 8%. A commercially available source of magnesium ions comprises about 5%, as shown in Example 1.

Any source and amount of sodium or sodium ions may be used. A preferred source of sodium ions is a soluble sodium composition, more preferably a sodium oxide. The amount of sodium ions present in the composition may range from about 1% to about 20%, preferably from about 2% to about 10%, more preferably from about 3% to about 9%. A commercially available source of sodium ions comprises about 6%, as shown in Example 1.

Any source and amount of phosphorus or phosphorus ions may be used. A preferred source of phosphorus ions is a soluble phosphorus composition, more preferably a phosphorus oxide. The amount of phosphorus ions present in the composition may range from about 1% to about 20%, preferably from about 2% to about 10%, more preferably from about 3% to about 7%. A commercially available source of phosphorus ions comprises about 4%, as shown in Example 1.

Any source and amount of strontium or strontium ions may be used. A preferred source of strontium ions is a soluble strontium composition, more preferably a strontium oxide. The amount of strontium ions present in the composition may range from about 0% to about 5%, preferably from about 0.05% to about 3%, more preferably from about 0.05% to about 1%. A commercially available source of strontium ions comprises about 0.1%, as shown in Example 1.

Any source and amount of zinc or zinc ions may be used. A preferred source of zinc ions is a soluble zinc composition, more preferably a zinc oxide. The amount of zinc ions present in the composition may range from about 0% to about 10%, preferably from about 0.05% to about 5%, more preferably from about 0.05% to about 3%. A commercially available source of zinc ions comprises about 1%, as shown in Example 1.

Any source and amount of iron or iron ions may be used. A preferred source of iron ions is a soluble iron composition, more preferably an iron oxide. The amount of iron ions present in the composition may range from about 0% to about 5%, preferably from about 0.05% to about 3%, more preferably from about 0.05% to about 1%. A commercially available source of iron ions comprises about 0.1%, as shown in Example 1.

An embodiment of the invention includes the use of a treatment composition comprising a source of boron or boron ions, a source of copper or copper ions, and a source of calcium or calcium ions. The amount and form of the ions are described above.

An embodiment of the invention includes the use of a treatment composition comprising a source of boron or boron ions, a source of copper or copper ions, and a source of potassium or potassium ions. The amount and form of the ions are described above.

An embodiment of the invention includes the use of a treatment composition comprising a source of boron or boron ions, a source of copper or copper ions, and a source of magnesium or magnesium ions. The amount and form of the ions are described above.

An embodiment of the invention includes the use of a treatment composition comprising a source of boron or boron ions, a source of copper or copper ions, and a source of sodium or sodium ions. The amount and form of the ions are described above.

An embodiment of the invention includes the use of a treatment composition comprising a source of boron or boron ions, a source of copper or copper ions, and a source of phosphorus or phosphorus ions. The amount and form of the ions are described above.

In preferred embodiment of the invention, the treatment composition is mildly acidic, preferably has a pH above about 7, more preferably above about 9.

The tissue may be soaked in or exposed to the treatment composition for a period of time sufficient to achieve the beneficial results or characteristics listed in more detail below. One skilled in the art will recognize that the period or time required to achieve this result may vary based on the specific reagents and/or reaction conditions. The inventors have found that a period between about one and about sixty minutes is sufficient.

The inventor has found that treating tissue or biomaterial with a treatment composition of the present invention provides one or more beneficial results or characteristics, including but not limited to: good or improved capillary bed formation; good, improved, or promotes native tissue to invade or remodel wound site; maintain or improves one or more ECM components; improves or maintains one or more cytokines; improves or maintains granulation; promotes granulation within about two to about three days; promotes native tissue growth at the wound site from the margin(s) toward the center; improves or maintains a collagen matrix with good or improved ECM; improves or maintains a collagen or ECM matrix with one or more epitopes for cellular attachment; promotes, maintains, or provides one or more growth factors; promotes, maintains, or provides vascularization; and promotes, stimulates, maintains, or provides cellular bed vascularization.

An embodiment of the invention is tissue treated as described above and in dried form.

An embodiment of the invention is tissue treated as described above and in powder or granulated form.

An embodiment of the invention is a tissue or biomaterial treated with a treatment composition as described herein and formed into a sheet or patch material, including but not limited to dural or bladder patches or patching. Optionally, the sheet or patch material may be pulverized or powderized.

An embodiment of the invention includes a patch or patch-like material suitable for use in ophthalmic applications, including but not limited to a corneal patch.

An embodiment of the invention includes a composition of matter and it use in neural applications, including but not limited to a sheath or covering over a nerve or nerve structure.

A composition comprising tissue as described above may be used to treat human or animal wounds.

A composition as described above may be used to treat other non-would conditions. Exemplary conditions or uses include but are not limited to treating bone defects; as a patch (e.g. a skin graft, or repair of other body tissue defects); as a wrap or covering over an incision site.

In the embodiment in which the composition is used as a bulking agent, the composition may be used to treat urinary incontinence.

In one embodiment, the tissue as described above is used to treat a wound. Examples of these wounds include but are not limited to enucleation procedures, bone defects and bulking agents such as might be warranted in the treatment of urinary incontinence.

In alternative embodiments, the processes described above may further include one or more chemical or biological treatments to stabilize the tissue or biomaterial and to avoid or limit biochemical and structural degradation. Such additional treatments include but are not limited to the use of stabilizing solutions and/or solutions that prevent or reduce osmotic, hypoxic, autolytic, or proteolytic degradation; additional treatment(s) to protect against or reduce microbial contamination; and additional treatment(s) that protect against or reduce mechanical damage to the tissues or biomaterial.

One skilled in the art will recognize that the invention as described here may be reconfigured into different combinations, elements, and processes which are included within the scope of the invention.

The following provides exemplary methods and specific exemplary steps to illustrate the function of an apparatus and system according to the present invention

EXAMPLES

Example 1

Porcine small intestine is harvested by dissecting the entire small intestine tract fresh from an appropriate animal, preferably infection-free, preferably in the 150-200 Lb. range. The small intestine will measure approximately 20 feet in length. The jejunum of the intestine is identified and dissected away from the duodenum and ileum. While the duodenum and ileum may be processed in accordance to the teaching of this invention the jejunum is preferred. The jejunum is longitudinally dissected, and the mucosal lining is removed by mechanical scraping, such as with a razor blade. Care is taken not to cut the submucosa. Secondarily the serosal surface is cleaned and separated away. The jejunal submucosa is then washed by immersing in isotonic saline. A minimum of three washes are recommended. Washes are conducted at room temperature with stirring. Each wash will be approximately 15 minutes in length.

Once cleaned the washed tissue is ready to be treated with an antibiotic solution. One particularly useful antibiotic solution consists of: 1000 gms. Saline; 1.0 gm. Penicillin sodium salt; 0.0105 gm. Amphotericin B; 0.10 gm. Streptomycin sulfate.

The cleaned tissue is placed into the antibiotic solution at room temperature. Stirring is recommended and the tissue is processed in this manner for a minimum of 17 hours. Preparation of a Treatment Solution A salt solution is prepared using a stock salt solution of Avalon Medical's commercially available RediHeal wound treatment. RediHeal is a borate base bioceramic consisting of oxides of various salts including:

| Compound | Percent |
|---|---|
| $B_2O_3$ | 51.6 |
| CaO | 20.0 |

-continued

| Compound | Percent |
|---|---|
| $K_2O$ | 12.0 |
| MgO | 5.0 |
| $Na_2O$ | 6.0 |
| $P_2O_5$ | 4.0 |
| CuO | 0.40 (or 0.0) |
| Sr | 0.0 (or 0.1) |
| ZnO | 1.0 |
| $Fe_2O_3$ | 0.0 (or 0.1) |

In some formulations, copper is included (CuO, 0.40 above), and the mixture does not contain Sr (0.0) or $Fe_2O_3$ (0.0). In other formulations, copper is not used (0.0), and both Sr (0.1) and $Fe_2O_3$ (0.1) are included.

A 10% w/w solution of electrolyte solution may be prepared by adding 100 gr. RediHeal into distilled water (900 gms.) and mixing approximately 8 hours. The resulting solution is cloudy white and is filtered to separate the particulate.

SIS which has been cleaned and subjected to washing in an antibiotic solution in accordance to the described method is subsequently washed in a 0.9% saline solution a total of three times. Each wash is conducted for 15 minutes.

The washed SIS tissue is immersed into the salt solution. With stirring, the SIS becomes infused with the salt solution. One useful ratio of SIS tissue to salt solution is: –13 gms. (tamped) SIS/900 mL. electrolyte solution.

After stirring for a period of time, e.g., 1-45 minutes, the SIS is removed from the solution and placed onto a pin frame and the tissue is mildly stretched. The tissue/pin frame combination is frozen to –40 F. Alternately the tissue can be frozen using dry ice.

The tissue/pin frame is subsequently placed into a lyophilizer and the tissue is dried for a period of 2-12 hours or until such time that the tissue is dry. At this time the tissue appears white in color and is rigid in nature.

Subsequently the tissue is removed from the lyophilizer, trimmed to size, placed into an appropriate container and processed for sterilization. The tissue may be sterilized using any suitable or known technique or process, including but not limited to ETO or electron beam radiation.

Example 2. Powder/Ground SIS

A further useful embodiment of SIS relates to the need for the granularized or powder form of the tissue.

Tissue harvested from an appropriate source is cleaned as previously described. In order to form a powder form of the SIS material the following steps are conducted:

Cleaned, wet, processed tissue is macerated using a knife, razor, scissor etc. until pieces are small enough to be placed into a laboratory mill such as a Wiley mill.

Prior to milling the small pieces are frozen w/dry ice, or nitrogen.

The frozen pieces in tandem with the dry ice are forced thru and past the cutting edges of the mill. The resulting pieces will shear until they can drop through the screen size of the mill. The "powder" containing a quantity of dry ice is placed into a pan which can be then re-frozen and then further processed for lyophilization. The tissue is processed until a white, granular appearance is obvious.

Subsequently the powdered tissue is packaged for sterilization via e-beam or ETG. Sterile tissue processed to form powder is useful in the treatment of wounds in which a sheet for of SIS/salt is not conducive to use.

While the invention has been described in some detail by way of illustration and example, it should be understood that the invention is susceptible to various modifications and alternative forms, and is not restricted to the specific embodiments set forth in the Examples. It should be understood that these specific embodiments are not intended to limit the invention but, on the contrary, the intention is to cover all modifications, equivalents, and alternatives falling within the spirit and scope of the invention.

I claim:

1. A method of manufacturing a therapeutic biomaterial comprising:

contacting harvested donor tissue comprising an extracellular matrix (ECM) ex vivo with a treatment composition that comprises an aqueous electrolyte solution with a source of boron ions and a source of copper ions, wherein the harvested donor tissue is contacted with the treatment composition for a period between about one and about sixty minutes.

2. The method of claim 1, wherein the source of boron ions comprises up to about 80% of the composition.

3. The method of claim 1, wherein the source of copper ions comprises up to about 5% of the composition.

4. The method of claim 1, wherein the treatment composition further comprises one or more of the following ingredients:

a source of calcium;

a source of potassium;

a source a magnesium; a source of sodium;

a source of phosphorus; ionic forms or any of the above;

oxide forms of any of the above;

a source of strontium;

a source of zinc; a source of iron;

ionic forms of strontium, zinc, or iron; oxide forms of strontium, zinc, or iron; and any of the ingredients listed above alone or in any combination.

5. The method of claim 1, wherein the treatment composition comprises:

a boron oxide and a copper oxide; and at least one of an oxide of calcium, potassium, magnesium, sodium, or phosphorus.

6. The method of claim 1, wherein the treatment composition is an electrolyte composition with a conductivity ranging from 1 to 20 mS/cm.

7. The method of claim 1, wherein the harvested donor tissue is selected from the group consisting of submucosa tissues, renal capsule membrane, amnion, dura matter, pericardium, serosa, and peritoneum or basement membrane.

8. The method of claim 1, wherein the harvested donor tissue is intestinal submucosa tissue.

9. The method of claim 8, wherein the harvested donor tissue is urinary bladder matrix.

10. The method of claim 1, wherein the harvested donor tissue is derived from an animal or human source.

11. The method of claim 1, further comprising contacting the harvested donor tissue with an antimicrobial composition prior to contacting with the treatment composition.

12. A method of treating a biomaterial ex vivo comprising:

harvesting donor tissue from a human or animal donor; and contacting the harvested donor tissue ex vivo with a treatment composition that comprises an electrolyte solution with a source of boron ions and a source of copper ions.

13. The method of claim 12, wherein the harvested donor tissue is selected from the group consisting of an extracellular matrix (ECM)-containing material, submucosa tissues, intestinal submucosa tissue, renal capsule membrane, amnion, dura matter, pericardium, serosa, and peritoneum or basement membrane.

14. The method of claim 12, wherein the harvested donor tissue is small intestinal submucosa tissue.

15. The method of claim 12, further comprising contacting the harvested donor tissue with an antimicrobial composition prior to contacting with the treatment composition.

16. The method of claim 12, wherein the harvested donor tissue is contacted with the treatment composition for a period between about 1 minute to about 60 minutes.

17. A method of treating a biomaterial ex vivo comprising:

obtaining a harvested donor tissue from a human or animal donor; and contacting the harvested donor tissue ex vivo with a treatment composition that comprises an electrolyte solution with a source of boron ions and a source of copper ions.

18. The method of claim 17, wherein the harvested donor tissue is selected from the group consisting of an extracellular matrix (ECM)-containing material, submucosa tissues, intestinal submucosa tissue, renal capsule membrane, amnion, dura matter, pericardium, serosa, and peritoneum or basement membrane.

19. The method of claim 17, wherein the harvested donor tissue is small intestinal submucosa tissue.

20. The method of claim 17, further comprising contacting the harvested donor tissue with an antimicrobial composition prior to contacting with the treatment composition.

* * * * *